United States Patent [19]

Tomita et al.

[11] Patent Number: 5,424,396
[45] Date of Patent: Jun. 13, 1995

[54] ANTIMICROBIAL PEPTIDE AND ANTIMICROBIAL AGENT

[75] Inventors: Mamoru Tomita, Kanagawa; Kozo Kawase; Mitsunori Takase, both of Saitama; Wayne R. Bellamy, Kanagawa; Koji Yamauchi, Kanagawa; Hiroyuki Wakabayashi, Kanagawa; Yukiko Tokita, Kanagawa, all of Japan

[73] Assignee: Morinaga Milk Industry Co., Ltd., Tokyo, Japan

[21] Appl. No.: 165,545

[22] Filed: Dec. 13, 1993

Related U.S. Application Data

[63] Continuation of Ser. No. 871,981, Apr. 22, 1992, abandoned.

[30] Foreign Application Priority Data

Apr. 24, 1991 [JP] Japan .................................. 3-094494

[51] Int. Cl.⁶ .......................... C07K 7/06; C07K 7/00; A61K 38/00
[52] U.S. Cl. .................................. 530/329; 530/330; 530/331
[58] Field of Search .............................. 530/329–330, 530/331; 514/17–18

[56] References Cited

FOREIGN PATENT DOCUMENTS 0474506 11/1992 European Pat. Off. .
WO90/13642 11/1990 WIPO .

OTHER PUBLICATIONS

Rey, et al, *Nucleic Acids Res*, vol. 18, No. 17, 1990, p. 5288.
Powell, et al, *Nucleic Acids Res*, vol. 18, No. 13, 1990, p. 4013.
Klumpp, et al, *J. Bacteriology* vol. 170, No. 6, pp. 2763–2769 1988.

*Primary Examiner*—Jill Warden
*Assistant Examiner*—S. G. Marshall
*Attorney, Agent, or Firm*—Wenderoth, Lind & Ponack

[57] ABSTRACT

An antimicrobial peptide containing an amino acid sequence comprising at least from three to six arbitrary amino acid residues, or a derivative thereof, an antimicrobial agent containing said antimicrobial peptide or a derivative thereof as active components at a concentration of at least 2 μM, an antimicrobial composition containing said antimicrobial peptide or a derivative thereof, and a method for processing products which uses the antimicrobial agent containing at least said antimicrobial peptide or a derivative thereof.

8 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

Phe Gln Trp Gln Arg Asn (2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:2:

Phe Gln Trp Gln Arg
1                  5

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:

(B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:3:

Gln Trp Gln Arg
1

(2) INFORMATION FOR SEQ ID NO:4:

(i) SEQUENCE CHARACTERISTICS:
                (A) LENGTH: 3 amino acids
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:

-continued ( C ) IDENTIFICATION METHOD:
             ( D ) OTHER INFORMATION:

( x ) PUBLICATION INFORMATION:
             ( A ) AUTHORS:
             ( B ) TITLE:
             ( C ) JOURNAL:
             ( D ) VOLUME:
             ( E ) ISSUE:
             ( F ) PAGES:
             ( G ) DATE:
             ( H ) DOCUMENT NUMBER:
             ( I ) FILING DATE:
             ( J ) PUBLICATION DATE:
             ( K ) RELEVANT RESIDUES IN SEQ ID NO:

( x i ) SEQUENCE DESCRIPTION: SEQ ID NO:4:

Trp Gln Arg
 1

( 2 ) INFORMATION FOR SEQ ID NO:5:

( i ) SEQUENCE CHARACTERISTICS:
             ( A ) LENGTH: 5 amino acids
             ( B ) TYPE: amino acid
             ( C ) STRANDEDNESS: single
             ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
             ( A ) ORGANISM:
             ( B ) STRAIN:
             ( C ) INDIVIDUAL ISOLATE:
             ( D ) DEVELOPMENTAL STAGE:
             ( E ) HAPLOTYPE:
             ( F ) TISSUE TYPE:
             ( G ) CELL TYPE:
             ( H ) CELL LINE:
             ( I ) ORGANELLE:

( v i i ) IMMEDIATE SOURCE:
             ( A ) LIBRARY:
             ( B ) CLONE:

( v i i i ) POSITION IN GENOME:
             ( A ) CHROMOSOME/SEGMENT:
             ( B ) MAP POSITION:
             ( C ) UNITS:

( i x ) FEATURE:
             ( A ) NAME/KEY:
             ( B ) LOCATION:
             ( C ) IDENTIFICATION METHOD:
             ( D ) OTHER INFORMATION:

( x ) PUBLICATION INFORMATION:
             ( A ) AUTHORS:
             ( B ) TITLE:
             ( C ) JOURNAL:
             ( D ) VOLUME:
             ( E ) ISSUE:
             ( F ) PAGES:
             ( G ) DATE:
             ( H ) DOCUMENT NUMBER:
             ( I ) FILING DATE:
             ( J ) PUBLICATION DATE:
             ( K ) RELEVANT RESIDUES IN SEQ ID NO:

( x i ) SEQUENCE DESCRIPTION: SEQ ID NO:5:

Arg Arg Trp Gln Trp
 1               5

( 2 ) INFORMATION FOR SEQ ID NO:6:

( i ) SEQUENCE CHARACTERISTICS:
          ( A ) LENGTH: 4 amino acids
          ( B ) TYPE: amino acid
          ( C ) STRANDEDNESS: single
          ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
          ( A ) ORGANISM:
          ( B ) STRAIN:
          ( C ) INDIVIDUAL ISOLATE:
          ( D ) DEVELOPMENTAL STAGE:
          ( E ) HAPLOTYPE:
          ( F ) TISSUE TYPE:
          ( G ) CELL TYPE:
          ( H ) CELL LINE:
          ( I ) ORGANELLE:

( v i i ) IMMEDIATE SOURCE:
          ( A ) LIBRARY:
          ( B ) CLONE:

( v i i i ) POSITION IN GENOME:
          ( A ) CHROMOSOME/SEGMENT:
          ( B ) MAP POSITION:
          ( C ) UNITS:

( i x ) FEATURE:
          ( A ) NAME/KEY:
          ( B ) LOCATION:
          ( C ) IDENTIFICATION METHOD:
          ( D ) OTHER INFORMATION:

( x ) PUBLICATION INFORMATION:
          ( A ) AUTHORS:
          ( B ) TITLE:
          ( C ) JOURNAL:
          ( D ) VOLUME:
          ( E ) ISSUE:
          ( F ) PAGES:
          ( G ) DATE:
          ( H ) DOCUMENT NUMBER:
          ( I ) FILING DATE:
          ( J ) PUBLICATION DATE:
          ( K ) RELEVANT RESIDUES IN SEQ ID NO:

( x i ) SEQUENCE DESCRIPTION: SEQ ID NO:6:

Arg Arg Trp Gln
1

( 2 ) INFORMATION FOR SEQ ID NO:7:

( i ) SEQUENCE CHARACTERISTICS:
          ( A ) LENGTH: 4 amino acids
          ( B ) TYPE: amino acid
          ( C ) STRANDEDNESS: single
          ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
          ( A ) ORGANISM:
          ( B ) STRAIN:
          ( C ) INDIVIDUAL ISOLATE:

(D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY:
                    (B) LOCATION:
                    (C) IDENTIFICATION METHOD:
                    (D) OTHER INFORMATION:

(x) PUBLICATION INFORMATION:
                    (A) AUTHORS:
                    (B) TITLE:
                    (C) JOURNAL:
                    (D) VOLUME:
                    (E) ISSUE:
                    (F) PAGES:
                    (G) DATE:
                    (H) DOCUMENT NUMBER:
                    (I) FILING DATE:
                    (J) PUBLICATION DATE:
                    (K) RELEVANT RESIDUES IN SEQ ID NO:

(xi) SEQUENCE DESCRIPTION: SEQ ID NO:7:

Trp Gln Trp Arg
 1

(2) INFORMATION FOR SEQ ID NO:8:

(i) SEQUENCE CHARACTERISTICS:
                    (A) LENGTH: 3 amino acids
                    (B) TYPE: amino acid
                    (C) STRANDEDNESS: single
                    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY:
                    (B) LOCATION:
                    (C) IDENTIFICATION METHOD:
                    (D) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:8:

```
Gln Trp Arg
  1
```

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:9:

```
Leu Arg Trp Gln Asn Asp
  1               5
```

( 2 ) INFORMATION FOR SEQ ID NO:10:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:10:

Leu Arg Trp Gln Asn
 1                   5

( 2 ) INFORMATION FOR SEQ ID NO:11:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:

(F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:11:

Leu Arg Trp Gln
 1

(2) INFORMATION FOR SEQ ID NO:12:

(i) SEQUENCE CHARACTERISTICS:
                (A) LENGTH: 3 amino acids
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:

(A) AUTHORS:
                    (B) TITLE:
                    (C) JOURNAL:
                    (D) VOLUME:
                    (E) ISSUE:
                    (F) PAGES:
                    (G) DATE:
                    (H) DOCUMENT NUMBER:
                    (I) FILING DATE:
                    (J) PUBLICATION DATE:
                    (K) RELEVANT RESIDUES IN SEQ ID NO:

(xi) SEQUENCE DESCRIPTION: SEQ ID NO:12:

Arg Trp Gln
 1

(2) INFORMATION FOR SEQ ID NO:13:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION: 6
                (C) IDENTIFICATION METHOD:
                (D) OTHER INFORMATION: /note="Asn-NH2"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:13:

Phe Gln Trp Gln Arg Xaa
 1               5

ANTIMICROBIAL PEPTIDE AND ANTIMICROBIAL AGENT

This application is a continuation of application Ser. No. 07/871,981, filed Apr. 22, 1992, now abandoned.

FIELD OF THE INVENTION

The present invention concerns an antimicrobial peptide and an antimicrobial agent. More specifically, it concerns an antimicrobial agent and an antimicrobial composition containing a novel antimicrobial peptide [LACTOFERRICIN(trademark)] or a derivative of this peptide, as active components, in addition to a method for treating products which uses this antimicrobial agent.

In the specification of the present invention, the amino acide and peptide are represented by the abbreviations employed by IUPAC-IUB Committee on Biochemical Nomenclature, such as the following abbreviations.

Ala-: L-Alanine residue
Arg-: L-Arginine residue
Asn-: L-Asparagine residue
Asp-: L-Aspartic acid residue
Cys-: L-Cysteine residue
Gln-: L-Glutamine residue
Glu-: L-Glutamic acid residue
Gly-: Glycine residue
His-: L-Histidine residue
Ile-: L-Isoleucine residue
Leu-: L-Leucine residue
Lys-: -Lysine residue
Mct-: L-Methionine residue
Phe-: L-Phenylalanine residue
Pro-: L-Proline residue
Ser-: L-Serine residue
Thr-: L-Threonine residue
Trp-: L-Tryptophan residue
Tyr-: L-Tyrosine residue
Val-: L-Valine residue

PRIOR ART

Numerous inventions concerning peptides or their derivatives which possess antimicrobial properties against various microorganisms have so far been reported. Examples include a phosphonotripeptide (Japanese Patent Provisional Publications No.106689/82), a phosphonodipeptide derivative (Japanese Patent Provisional Publication No.13594/83) and a cyclic peptide derivative (Japanese Patent Provisional Publication No.213744/83) effective against Gram-positive and Gram-negative bacteria, a peptide demonstrating an antimicrobial and antiviral action (Japanese Patent Provisional Publication No.51247/84), a polypeptide effective against yeast (Japanese Patent Provisional Publication No.130599/85), a glycopeptide derivative effective against Gram-positive bacteria (Japanese Patent Provisional Publication No.172998/85, Japanese Patent Provisional Publication No.251699/86, Japanese Patent Provisional Publication No.44598/88), an oligopeptide effective against Gram-positive bacteria (Japanese Patent Provisional Publication No.22798/87), a peptide-like antibiotic substance (Japanese Patent Provisional Publication No.51697/87, Japanese Patent Provisional Publication No.17897/88) as well as an antimicrobial peptide extracted from blood cells of North American king crabs (Japanese Patent Provisional Publication No.53799/90) and an antimicrobial peptide isolated from blood lymph of honeybees (Japanese Patent Provisional Publication No.500084/90).

On the other hand, lactoferrin (hereinafter referred to as "LF"), which is a natural iron-binding protein contained in tears, saliva, peripheral blood, milk, etc. is known to demonstrate an antimicrobial activity against Escherichia coli, Candida, Clostridium and other potentially harmful microorganisms (Journal of Pediatrics, Vol. 94, p. 1, 1979). However, an antimicrobial effect of a peptide having a specific amino acid sequence which can be isolated from LF hydrolysate has not been described in any article, and therefore, was previously unknown. Furthermore, the specific amino acid sequence of said peptide having an antimicrobial effect was previously unknown.

The inventors of the present invention, in planning to cheaply isolate from nature a substance which possesses strong antimicrobial properties, which has no undesirable side effects (such as antigenicity) and is heat-resistant, focused on whey, a by-product of cheese manufacturing, and conducted research regarding the antimicrobial properties of LF contained in it. Surprisingly, they discovered that catabolites of LP produced by acid hydrolysis or by enzymatic cleavage of this protein have stronger antimicrobial properties and are more heat resistant than non-hydrolyzed LF, and have succeeded to isolate and synthesize potent antimicrobial peptide possessing specific amino acid sequences, and have filed a patent application (U.S. patent application Ser. No. 07/755,161). Previously, the amino acid sequences of these novel antimicrobial peptides have not been sufficiently understood, however, and, therefore, the development of an effective antimicrobial agent had not yet been achieved.

SUMMARY OF THE INVENTION

The objective of the present invention is to provide a novel antimicrobial peptide or a derivative thereof having a specific amino acid sequence which can be isolated from LF hydrolysate or chemically synthesized, and an antimicrobial agent, and an antimicrobial composition containing this peptide or its derivative as an active component, and a method for treating products which uses this antimicrobial agent.

The present invention provides:

(1) an antimicrobial peptide containing at least one of the following amino acid sequences (a)~(1), or a derivative thereof, (2) an antimicrobial agent containing an antimicrobial substance selected from the group consisting of an antimicrobial peptide which contains at least one of the following amino acid sequences (a)~(1) or a derivative thereof, and pharmaceutically or sitologically approved salts thereof, or a mixture thereof, as active components, (3) a method for treating products which uses this antimicrobial agent, and (4) an antimicrobial composition containing an antimicrobial substance selected from the group consisting of an antimicrobial peptide which contains at least one of the following amino acid sequences (a)~(1) or a derivative thereof, and pharmaceutically or sitologically approved salts thereof, or a mixture thereof, as active components.

---

(a)   Phe—Gln—Try—Gln—Arg—Aan   (SEQ ID NO. 1)

-continued

| | | |
|---|---|---|
| (b) | Phe—Gln—Trp—Gln—Arg | (SEQ ID NO. 2) |
| (c) | Gln—Trp—Gln—Arg | (SEQ ID NO. 3) |
| (d) | Trp—Gln—Arg | (SEQ ID NO. 4) |
| (e) | Arg—Arg—Trp—Gln—Trp | (SEQ ID NO. 5) |
| (f) | Arg—Arg—Trp—Gln | (SEQ ID NO. 6) |
| (g) | Trp—Glu—Trp—Arg | (SEQ ID NO. 7) |
| (h) | Gln—Trp—Arg | (SEQ ID NO. 8) |
| (i) | Leu—Arg—Trp—Gln—Asn—Asp | (SEQ ID NO. 9) |
| (j) | Leu—Arg—Trp—Gln—Asn | (SEQ ID NO. 10) |
| (k) | Leu—Arg—Trp—Gln | (SEQ ID NO. 11) |
| (l) | Arg—Trp—Gln | (SEQ ID NO. 12) |

DETAILED DESCRIPTION OF THE INVENTION

The antimicrobial peptide or the derivative thereof of the present invention may be prepared by enzymatic hydrolysis of bovine LF isolated by the conventional method from cow's milk or a commercially available LF. The antimicrobial peptide derivatives are those derivatives having minor amino acid partial substitutions or additions which do not abolish the antimicrobial properties of the peptide.

Alternatively, the antimicrobial peptide of the present invention can be chemically synthesized, and an example of chemical synthesis of the peptide is as follows. Using an automated peptide synthesizer (such as the one manufactured by Pharmacia LKB Biotechnology Co., LKB Biolynk 4170), the peptide is synthesized following the solid-phase peptide synthesis method of Sheppard et al. (Journal of Chemical Society Perkin I, p. 538, 1981). N,N'-dicyclohexylcarbodiimide is added to amino acids whose amine functional groups are protected by 9-fluorenylmethoxycarbonyl (Fmoc) groups (hereinafter referred to as "Fmoc-amino acid") and anhydrides of the desired amino acids are produced, and these Fmoc-amino acid anhydrides are used for synthesis. In order to produce a peptide chain, an Fmoc-amino acid anhydride corresponding to the C-terminal amino acid residue is fixed to Ultrosyn A resin (manufactured by Pharmacia LKB Biotechnology Co.) through the carboxyl group thereof, using dimethylaminopyridine as a catalyst. Next, the resin is washed with dimethylformamide containing piperidine, and the protecting group of the amino functional group of the C-terminal amino acid is removed. Next, and Fmoc-amino acid anhydride corresponding to the amino acid residue which is second from the C-terminal of the amino acid sequence of the desired peptide is coupled to the unprotected amine functional group of the first amino acid fixed to the resin through the above-mentioned C-terminal amino acid residue. Subsequently the successive desired amino acid are fixed in the same. After coupling of all the amino acids is completed and the peptide chain of the desired amino acid sequence is formed, the protective groups other than acetoamidomethyl are removed and the peptide is released with a solvent [composed of, for example, 94%(weight, the same hereinafter unless otherwise indicated) trifluoroacetic acid, 5% phenol and 1% ethandiol], and the peptide is purified using high-performance liquid chromotography.

As an example of the antimicrobial peptide derivative of the present invention, a peptide having an amide at the carboxyl end is prepared as follows: fixing sequentially amino acid residues in the same manner as in the example mentioned above except for using Ultrosyn B resin (manufactured by Pharmacia LKB Biotechnology Co.); after the total completion of coupling of amino acid and the resultant formation of a peptide chain having a desired amino acid sequence, eliminating the protecting groups other than acetoamidemethyl by means of a solvent which comprises 94% trifluoroacetic acid, 5% phenol, and 1% ethandiol; then isolating peptides from the resin by means of a saturated ammonia/methanol solvent; and purifying peptides using high-performance liquid chromatography.

The antimicrobial peptide so obtained, the pharmaceutically or sitologically approved salts thereof, or a mixture of at least two of the above, is included as active components at a concentration of at least 2 micromoles per kg and preferably 5 to 20 micromoles per kg, in order to obtain the antimicrobial agent or the antimicrobial composition of the present invention. Also, in the case of using the antimicrobial peptide derivative, the antimicrobial agent or composition can be obtained in the same manner as described above.

The antimicrobial peptide or derivative thereof of the present invention can be administered to humans or to animals without further modifications, can be used in food products, medicinal pharmaceutical products (such as eye medications, mastitis medications, diarrhea medications and athlete's foot medications), non-medicinal pharmaceutical products (such as mouth washes, antiperspirants and hair tonics), various cosmetic products (such as hair conditioners), various tooth-brushing products (such as toothpastes and toothbrushes), various feminine hygiene products, various baby products (such as diapers), various geriatric products (such as denture cement and diapers), various cleaning agents (such as soaps, medicinal soaps, shampoos, rinses, laundry detergents, kitchen detergents and house detergents), various sterilized products (such as sterilized kitchen paper and sterilized toilet paper), feed and materials which serve as raw materials of the above, and they can also be added to, compounded with, sprayed onto, adhered to or used for coating or impregnation of any and all products wherein prevention or inhibition of microbial proliferation is generally desired.

The antimicrobial peptide or derivative thereof of the present invention can be used individually or concomitantly with other antimicrobial agents for treating any and all products wherein prevention or inhibition of microbial proliferation is generally desired, for example, food products, medicinal pharmaceutical products (such as eye medications, mastitis medications, diarrhea medications and athlete's foot medications), non-medicinal pharmaceutical products (such as mouth washes, antiperspirants and hair tonics), various cosmetic products (such as hair conditioners), various tooth-brushing products (such as toothpastes and toothbrushes), various feminine hygiene products, various baby products (such as diapers), various geriatric products (such as denture cement and diapers), various cleaning agents (such as soaps, medicinal soaps, shampoos, rinses, laundry detergents, kitchen detergents and house detergents), various sterilized products (such as sterilized kitchen paper and sterilized toilet paper), feed and materials which serve as raw materials of the above.

Next, the present invention will be described in detail by means of Experiments.

EXPERIMENT 1

This experiment was performed in order to study the antimicrobial activity of an antimicrobial peptide.

(1) Sample preparation

Samples of Nos. 1 to 12 were chemically synthesized using the same methods as in Examples 1 to 12, respectively.

(2) Experimental method

1. Preparation of a pre-incubation solution

One platinum loop was collected from a stock slant of *Escherichia coli*, streaked on a standard agar medium (manufactured by Nissui Pharmaceutical Co.) and incubated under aerobic conditions for 16 hours at 37° C., the colonies which grew on the surface of the standard agar medium were collected using a platinum loop, suspended in sterilized physiological saline solution, the turbidity was measured using a spectrophotometer (manufactured by Hitachi Manufacturing Co.) and adjusted to 0.1 (O.D.; 660 nm) and a pre-incubation solution was prepared.

2. Preparation of a basal medium

Bactocasitone (manufactured by Difco Laboratory Co.) was dissolved at a concentration of 1% in purified water, the pH was adjusted to 7.0 with 1M sodium hydroxide, the solution was sterilized at 115° C. for 15 minutes and a basal medium (liquid medium) was prepared.

3. Preparation of the test media and of the control medium

Each sample was dissolved at a concentration of 0.01% in purified water, sterilization was performed by using a sterilization filter (manufactured by Advantek Co.) and test media, prepared by adding samples at concentrations of 0.5, 1, 2, 5, 10, 20, 50, 100 and 200 micromol ($\mu$M) to the basal medium, as well as a control medium with no added samples, were prepared.

4. Antimicrobial activity test

The above-mentioned pre-incubation solution was inoculated into the above-mentioned test media and the control medium at a concentration of 1%, cultured under aerobic conditions for 16 hours at 37° C., the turbidities of the culture media were measured using the above-mentioned method and the rate of inhibition of *E. coli* proliferation was calculated according to the following formula.

*rate of inhibition of proliferation* (%) = 100 (1 − A/B)

wherein A is the difference in turbidity of the test culture medium (the difference between the turbidity of the test culture medium after 16 hours of culture and the turbidity of the test culture medium before the culturing) and B is the turbidity of the control medium (the difference between the turbidity of the control culture medium after 16 hours of culture and the turbidity of the control culture medium before the culturing). The percentages of the rate of inhibition of proliferation are not in weight (same hereinafter).

(3) Results

The results of this experiment are shown in Table 1. As is clear from Table 1, all the samples Nos. 1 to 12 had an antimicrobial activity at concentration of 2 $\mu$M, and a high antimicrobial activity within a range of 10 to 50 $\mu$M. At concentrations over 100 $\mu$M, such increase in concentration did not lead to increased antimicrobial activity. Antimicrobial activity of each peptide is therefore available at a concentration of at least 2 $\mu$M, and more preferably, within a range of 10 to 50 $\mu$M. Antimicrobial activity within this quantity range is almost equal to that of aminobenzyl-penicillin.

EXPERIMENT 2

This experiment was performed in order to determine the amino acid sequence of the antimicrobial peptide used in Experiment 1.

The peptides of sample Nos. 1 to 12 used in Experiment 1 were hydrolyzed by 6N hydrochloric acid and the amino acid compositions were analyzed by conventional methods, using an amino acid analyzer. Given cycles of Edman's degradation were performed on each sample, using a gas-phase sequencer (manufactured by Applied Biosystems Co.), and sequences of amino acid residues was determined.

As a result it was determined that these peptides consisted of 3 to 6 amino acid residues, and formed the following amino acid sequence.

Sample No. 1: Phe-Gln-Trp-Gln-Arg-Asn
Sample No. 2: Phe-Gln-Trp-Gln-Arg
Sample No. 3: Gln-Trp-Gln-Arg
Sample No. 4: Trp-Gln-Arg
Sample No. 5: Arg-Arg-Trp-Gln-Trp
Sample No. 6: Arg-Arg-Trp-Gln
Sample No. 7: Trp-Gln-Trp-Arg
Sample No. 8: Gln-Trp-Arg
Sample No. 9: Leu-Arg-Trp-Gln-Asn-Asp
Sample No. 10: Leu-Arg-Trp-Gln-Asn
Sample No. 11: Leu-Arg-Trp-Gln
Sample No. 12: Arg-Trp-Gln

EXPERIMENT 3

This experiment was performed to study the antimicrobial effect of an antimicrobial agent containing the peptide of the present invention.

Commercially available primary-processed vegetable (known as "cut vegetable") in an amount of 100 g was immersed in an aqueous solution for 30 seconds, in which the antimicrobial peptide synthesized in the same manner as in Example 5 was added at a concentration of 20 $\mu$M. After sufficiently eliminating water, the vegetable was held at 5° C., and the viable count was measured by the conventional method along with time lapse. Vegetable immersed in tap water with no antimicrobial peptide served as control.

The results of this experiment are shown in Table 2. As in clear from Table 2, proliferation of bacteria was remarkably inhibited in the vegetable treated with the antimicrobial agent of the present invention. Almost the same results were obtained also for antimicrobial peptides synthesized in the same manner as in the other Examples and the derivative thereof.

EXPERIMENT 4

This experiment was performed to study the preservative effect in foods mixed with the antimicrobial peptide of the present invention.

Milk was pasteurized at 65° C. for 30 minutes and poured separately into test tubes to an amount of 10 ml each. The antimicrobial peptide synthesized in the same manner as in Example 6 was added to the milk at a concentration of 30 $\mu$M, and the mixture was uniformly mixed, and closely sealed. Milk in a sealed test tube with no antimicrobial peptide served as control. All the test tubes were held at 25° C., and the number of days required for the milk to solidify was measured.

As a result, while all the milk containing the antimicrobial peptide solidified in ten days, the control solidified in two days. This suggests that the antimicrobial peptides of the present invention largely retarded solidification of milk. An organoleptic test carried out on the tested milk and the control before preservation showed no difference in flavor or in exterior view between the two groups. Similar results were obtained for antimicrobial peptides synthesized in the same manner as in the other Examples and the derivatives thereof.

EXPERIMENT 5

This experiment was performed to study the antimicrobial spectrum of the antimicrobial peptides and the derivatives thereof of the present invention.

(1) Sample preparation

The antimicrobial peptide (sample No. 1) was prepared using the same method as in Example 1, and antimicrobial peptide derivative (sample No. 16) was prepared using the same method as in Example 16, and were sterilized by filtration using a 0.45 µm Millex filter prior to use.

(2) Experimental methods

Various microbial strains shown in Table 3 in the logarithmic phase of growth were inoculated in a peptone medium which consisted of 1% Bactopeptone (manufactured by Difco Laboratory Co.) at a cell concentration of $10^6$/ml, and 160 µl thereof were incubated for 17 hours at 37° C. using a 96-hole microtiter plate (manufactured by Falcon Co.). Each sample was added to each medium at a ratio of 0, 1.5, 3, 6, 12, 25, 50, 100, 125 or 250 µM. The growth of the various microorganisms in the various samples at various concentrations was studied by measuring the light absorption at 660 nm. The minimum concentration of the antimicrobial peptide which completely inhibited the growth of the various microorganisms was considered the minimum inhibitory concentration (MIC: µM).

The microorganisms used in this experiment are available from Institute of Medical Science, University of Tokyo (IID), Japanese Physicochemical Laboratories (JCM), Japanese International Dairy Federation (IDF), and the storage at the laboratory of the applicant (MMI).

(3) Results

The results of this experiment are shown in Table 3. As is clear from Table 3, the antimicrobial peptide of sample No. 1 showed an antimicrobial activity at concentration of up to 250 µM against the tested Gram-positive bacteria, *Listeria monocytogenes* IDF 1b (represented by LM in the table) and *Staphylococcus aureus* JCM 2151 (represented by SA in the table).

Sample No. 16 which is the derivative of sample No. 1 showed a strong antimicrobial activity about 2 to 2.5 times as high as that of sample No. 1.

In addition, virtually identical results were obtained with the other antimicrobial peptides of the present invention, other antimicrobial peptides derivatives and salts thereof.

EFFECTS OF THE INVENTION

Since the antimicrobial peptide or derivative thereof of the present invention consists of low molecular weight, it possesses a potent antimicrobial activity without any antigenicity, and since it demonstrates an antimicrobial effect even in small amounts, it can be applied to food products etc. with hardly any effect on their flavor.

The present invention will now be explained in further detail by means of examples. Of course, the present invention is not limited to or by these examples.

EXAMPLE 1

A peptide was synthesized using an automated peptide synthesizer (manufactured by Pharmacia LKB Biotechnology Co., Trademark: LKB Biolynx 4710) in accordance with the solid-phase peptide synthesis method of Sheppard et al. (Journal of Chemical Society Perkin I, p. 536, 1981).

N,N'-dicyclohexylcarbodiimide was added to amino acids whose the amine functional groups were protected by Fmoc groups and anhydrides of the desired amino acids were produced, and these Fmoc-amino anhydrides were used for synthesis. In order to produce a peptide chain, about 0.1 mmol of Fmoc-asparagine anhydride corresponding to the C-terminal asparagine residue was fixed to 1 g of Ultrosyn A resin (manufactured by Pharmacia LKB Biotechnology Co.) through the carboxyl group thereof, using dimethylaminopyridine as a catalyst. Next, the resin in an amount of 1 g was washed with dimethylformamide containing piperidine, and the protecting group of the amine functional group of the C-terminal amino acid was removed. The Fmoc-arginine anhydride corresponding to the second amino acid residue from the C-terminal was then coupled to the unprotected amine functional group of the above-mentioned asparagine residue. Subsequently, glutamine, tryptophan, glutamine and phenylalanine were sequentially fixed in the same manner.

After the completion of coupling of all amino acids and formation of a peptide chain of the desired amino acid sequence, protecting groups other than acetoamidoemthyl were removed and the peptide was released with a solvent comprising 94% trifluoroacetic acid, 5% phenol and 1% ethandiol, the peptide was purified by using high-performance liquid chromatography. This solution was concentrated and dried, and about 7 mg of peptide having the amino acid sequene Phe-Gln-Trp-Gln-Arg-Asn was obtained.

EXAMPLE 2

About 8 mg of a peptide having the amino acid sequence Phe-Gln-Trp-Gln-Arg was obtained in the same manner as in Example 1 except that arginine, glutamine, tryptophan, glutamine and phenylalanine were fixed sequentially from the C-terminal.

EXAMPLE 3

About 3 mg of a peptide having the amino acid sequence Gln-Trp-Gln-Arg was obtained in the same manner as in Example 1 except that arginine, glutamine, tryptophan and glutamine were fixed sequentially from the C-terminal.

EXAMPLE 4

About 2 mg of peptide having the amino acid sequence Trp-Gln-Arg was obtained in the same manner as in Example 1 except that arginine, glutamine and tryptophan were fixed sequentially from the C-terminal.

EXAMPLE 5

About 11 mg of a peptide having the amino acid sequence Arg-Arg-Trp-Gln-Trp was obtained in the same manner as in Example 1 except that the tryptophan, glutamine, tryptophan, arginine and arginine were fixed sequentially from the C-terminal.

EXAMPLE 6

About 5 mg of a peptide having the amino acid sequence Arg-Arg-Trp-Gln was obtained in the same manner as in Example 1 except that glutamine, tryptophan, arginine and arginine were fixed sequentially from the C-terminal.

EXAMPLE 7

About 5 mg of a peptide having the amino acid sequence Trp-Gln-Trp-Arg was obtained in the same manner as in Example 1 except that arginine, tryptophan, glutamine and tryptophan were fixed sequentially from the C-terminal.

EXAMPLE 8

About 4 mg of a peptide having the amino acid sequence Gln-Trp-Arg was obtained in the same manner as in Example 1 except that arginine, tryptophan and glutamine were fixed sequentially from the C-terminal.

EXAMPLE 9

About 9 mg of a peptide having the amino acid sequence Leu-Arg-Trp-Gln-Asn-Asp was obtained in the same manner as in Example 1 except that aspartic acid, asparagine, glutamine, tryptophan, arginine and leucine were fixed sequentially from the C-terminal.

EXAMPLE 10

About 8 mg of a peptide having the amino acid sequence Leu-Arg-Trp-Gln-Asn was obtained in the same manner as in Example 1 except that asparagine, glutamine, tryptophan, arginine and leucine were fixed sequentially from the C-terminal.

EXAMPLE 11

About 6 mg of a peptide having the amino acid sequence Leu-Arg-Trp-Gln was obtained in the same manner as in Example 1 except that glutamine, tryptophan, arginine and leucine were fixed sequentially the C-terminal.

EXAMPLE 12

About 17 mg of a peptide having the amino acid sequence Arg-Trp-Gln was obtained in the same manner as in Example 1 except that glutamine, tryptophan and arginine were fixed sequentially from the C-terminal.

EXAMPLE 13

An antimicrobial peptide synthesized in the same manner as in Example 3 in an amount of 42 mg was added to 10 kg of a commercially available assorted feed for eel of the following composition, and the mixture was uniformly mixed to obtain an eel-raising feed:

| | |
|---|---|
| Fish meal | 63.0% |
| Wheat gluten | 5.0% |
| Brewer's yeast powder | 6.0% |
| Wheat powder | 22.4% |
| Vitamin mixture | 1.0% |
| 50% chloline chloride | 0.3% |
| Mineral mixture | 2.3% |

EXAMPLE 14

A hair rinse of the following composition was produced by the conventional method:

| | |
|---|---|
| dialkyldimethylammonium-Chloride | 2.1% |
| Ethanol | 1.1% |
| Polyoxyethylene stearyl ester | 1.1% |
| 1,3-butyleneglycol | 3.1% |
| Cationic cellulose | 0.2% |
| Antimicrobial peptide of Example 6 | 0.0006% |
| Purified water | 92.4% |

EXAMPLE 15

A drink of the following composition was produced by the conventional method:

| | |
|---|---|
| Dextrin | 3.0% |
| Fruit sugar | 2.5% |
| Calcium chloride | 0.005% |
| Common salt | 01065% |
| Dipotasium phosphate | 0.016% |
| Potassium carbonate | 0.027% |
| Vltanin C | 0.03% |
| Antimicrobial peptide of Example 6 | 0.0002% |
| Water | 94.4% |

EXAMPLE 16

Amino acid residues were sequentially fixed in the same manner as in Example 1 except for the use of Ultrosyn B resin (manufactured by Pharmacia LKB Co.). After the completion of coupling of all amino acids, the protecting group other than acetoamidomethyl were removed by means of a solvent comprising 94% trifluoroacetic acid, 5% phenol, and 1% ethandiol, and a peptide was released by the use of saturated ammonia/methanol solution. Then, the peptide was purified by high-performance liquid chromatography, concentrated and dried to obtain about 6 mg of a peptide derivative having the amino acid sequence Phe-Gln-Trp-Gln-Arg-Asn-NH$_2$.

EXAMPLE 17

A tooth-paste of the following composition was produced:

| | |
|---|---|
| Sorbitol | 47.0% |
| Glycerin | 15.0% |
| Carboxymethylcellulose sodium | 2.0% |
| Sorbitan ester of fatty acid | 1.0% |
| Saccharin sodium | 1.0% |
| Antimicrobial peptide derivative of Example 16 | 0.002% |

TABLE 1

| Sample No. | Added quantity (µM) and inhibitory rate (%) | | | | | | | | |
|---|---|---|---|---|---|---|---|---|---|
| | 0.5 | 1 | 2 | 5 | 10 | 20 | 60 | 100 | 200 |
| 1 | 0 | 13 | 20 | 45 | 88 | 94 | 100 | 100 | 100 |
| 2 | 0 | 3 | 14 | 40 | 72 | 92 | 100 | 100 | 100 |
| 3 | 0 | 5 | 11 | 35 | 63 | 83 | 98 | 100 | 100 |
| 4 | 0 | 0 | 8 | 30 | 58 | 77 | 92 | 100 | 100 |
| 5 | 0 | 59 | 83 | 94 | 100 | 100 | 100 | 100 | 100 |
| 6 | 0 | 32 | 75 | 88 | 98 | 100 | 100 | 100 | 100 |
| 7 | 0 | 21 | 68 | 83 | 95 | 100 | 100 | 100 | 100 |
| 8 | 0 | 8 | 40 | 72 | 84 | 93 | 100 | 100 | 100 |
| 9 | 0 | 32 | 51 | 79 | 89 | 100 | 100 | 100 | 100 |
| 10 | 0 | 11 | 31 | 75 | 88 | 100 | 100 | 100 | 100 |
| 11 | 0 | 4 | 10 | 40 | 67 | 85 | 100 | 100 | 100 |

TABLE 1-continued

| Sample | Added quantity (μM) and inhibitory rate (%) | | | | | | | | |
|---|---|---|---|---|---|---|---|---|---|
| No. | 0.5 | 1 | 2 | 5 | 10 | 20 | 60 | 100 | 200 |
| 12 | 0 | 3 | 6 | 25 | 48 | 79 | 100 | 100 | 100 |

TABLE 2

| Sample | Viable count/g (control) | | | |
|---|---|---|---|---|
| | 0 hr. | 22 hrs. | 24 hrs. | 36 hrs. |
| Control | $1.3 \times 10^3$ | $3.1 \times 10^4$ | $3.4 \times 10^5$ | $5.7 \times 10^5$ |
| The present invention | $1.3 \times 10^3$ | $1.6 \times 10^3$ | $2.0 \times 10^3$ | $2.3 \times 10^5$ |

TABLE 3

| Sample No. | Minimum inhibitory concentration (μM) | |
|---|---|---|
| | LM | SA |
| 1 | 100 | 250 |
| 16 | 50 | 100 |

What is claimed is:

1. A substantially purified and isolated peptide having antimicrobial activity consisting of an amino acid sequence selected from the group consisting of SEQ ID Nos. 1, 2, 3, 4, 5, 6, 7, 8, 9, 10, 11 and 12, or derivatives thereof having an amide at the carboxyl end thereof, which derivatives do not abolish the antimicrobial properties of the peptide.

2. A substantially purified and isolated peptide according to claim 1 in which the derivatives of said amino acid sequences are those having an amide at the carboxyl end thereof.

3. A substantially purified and isolated peptide having antimicrobial activity according to claim 1 which is prepared by chemical synthesis.

4. A substantially purified and isolated peptide having antimicrobial activity consisting of an amino acid sequence selected from the group consisting of SEQ ID Nos. 1, 2, 3, 4, 5, 6, 7, 8, 9, 10, 11 and 12.

5. An antimicrobial composition which comprises an antimicrobially effective amount of a substantially purified and isolated peptide having antimicrobial activity consisting of an amino acid sequence selected from the group consisting of SEQ ID Nos. 1, 2, 3, 4, 5, 6, 7, 8, 9, 10, 11 and 12, or derivatives thereof having an amide at the carboxyl end thereof, which derivatives do not abolish the antimicrobial properties of the peptide and a pharmacologically acceptable carrier therefor.

6. An antimicrobial composition according to claim 5 in which the derivatives of said amino acid sequences are those having an amide at the carboxyl end thereof.

7. An antimicrobial composition as claimed in claim 5, wherein the substantially purified and isolated peptide or derivatives thereof is contained in the composition at a concentration of at least 2 micromoles per kg.

8. An antimicrobial composition which comprises an antimicrobially effective amount of a substantially purified and isolated peptide having antimicrobial activity consisting of an amino acid sequence selected from the group consisting of SEQ ID Nos. 1, 2, 3, 4, 5, 6, 7, 8, 9, 10, 11 and 12 and a pharmacologically acceptable carrier therefor.

* * * * *